US008945159B2

(12) United States Patent  
Nussbaum (10) Patent No.: US 8,945,159 B2  
(45) Date of Patent: Feb. 3, 2015

(54) SURGICAL CLIP AND SURGICAL METHOD FOR TREATING AN ANEURYSUM

(71) Applicant: Eric S Nussbaum, St. Louis Park, MN (US)

(72) Inventor: Eric S Nussbaum, St. Louis Park, MN (US)

( * ) Notice: Subject to any disclaimer, the term of this patent is extended or adjusted under 35 U.S.C. 154(b) by 0 days.

(21) Appl. No.: 13/846,417

(22) Filed: Mar. 18, 2013

(65) Prior Publication Data

US 2013/0226206 A1 Aug. 29, 2013

Related U.S. Application Data

(62) Division of application No. 12/800,924, filed on May 24, 2010, now abandoned.

(51) Int. Cl.
*A61B 17/08* (2006.01)
*A61B 17/122* (2006.01)

(52) U.S. Cl.
CPC ........... *A61B 17/122* (2013.01); *A61B 17/1227* (2013.01)
USPC ...................................... 606/158

(58) Field of Classification Search
USPC ........... D8/52, 54; D24/143; 606/51, 52, 151, 606/157, 158, 205–209
See application file for complete search history.

(56) References Cited

U.S. PATENT DOCUMENTS

| | | | | |
|---|---|---|---|---|
| 2,491,050 A | * | 12/1949 | McAdoo | 606/151 |
| D246,190 S | | 10/1977 | Hodge | |
| 4,475,544 A | | 10/1984 | Reis | |
| 6,251,117 B1 | * | 6/2001 | Kringel et al. | 606/158 |
| 8,197,500 B2 | * | 6/2012 | Qi et al. | 606/157 |
| 2011/0288571 A1 | | 11/2011 | Steinhilper et al. | |

OTHER PUBLICATIONS

Application and File History for U.S. Appl. No. 12/800,924, filed May 24, 2010. Inventor: Eric S. Nussbaum.

* cited by examiner

*Primary Examiner* — Ashley Fishback
(74) *Attorney, Agent, or Firm* — Patterson Thuente Pedersen, P.A.

(57) ABSTRACT

An implantable aneurysm clip including a first arm and an opposed second arm. The first and second arms having corresponding opposed first and second clamping surfaces facing each other, and the first and second arms are movable relative to each other. The first and second clamping surfaces are shiftable between a first, preselected, open resting position in which the first and second clamping surfaces are separated by a first distance and a second open position wherein the first and second clamping surfaces are separated by a second distance. The second distance is greater than the first distance and the first and second clamping surfaces are biased toward the first position by a biasing force.

9 Claims, 6 Drawing Sheets

SURGICAL CLIP AND SURGICAL METHOD FOR TREATING AN ANEURYSUM

CLAIM TO PRIORITY

This application is a divisional of U.S. patent application Ser. No. 12/800,924 entitled "Surgical Clip and Surgical Method for Treating an Aneurysm" filed May 24, 2010, the entire contents of which are incorporated herein by reference.

FIELD OF THE INVENTION

The present invention relates in general to a surgical clip and, more specifically, to a surgical clip comprising a first arm and a second arm, the first and second arms having first and second clamping surfaces facing each other, and the first and second arms being mounted for movement relative to each other.

The present invention also relates, in general, to a surgical method for treating an aneurysm and, more specifically, to a surgical method for treating an aneurysm, the method comprising: applying a surgical clip to the aneurysm, the clip comprising a first arm and a second arm, the first and second arms having first and second clamping surfaces facing each other for clamping the aneurysm therebetween, and the first and second arms being mounted for movement relative to each other.

BACKGROUND OF THE INVENTION

Aneurysms are abnormal dilatations of blood vessels. A critical type of aneurysm is a brain aneurysm which is an abnormal dilatation of one of the blood vessels supplying blood flow to the brain itself. Aneurysms are felt to start as an area of potential weakness in the wall of the artery and typically occur at an arterial branch point. Over time, the natural pulsation of blood against the area of weakness can gradually cause the weakened area to dilate or enlarge. This process may be analogized to inflating a balloon. As the balloon stretches, the wall of the balloon typically becomes thinner. Eventually, if the wall is stretched too thin, the balloon bursts.

Similarly, if an aneurysm becomes too thin, the wall bursts allowing blood to escape from the blood vessels, in particular, the arteries in which the blood is supposed to be contained. The blood spills into the subarachnoid space, a potential space surrounding the brain that is normally filled with cerebrospinal fluid. This aneurysm bleeding or rupture results in what is known as a subarachnoid hemorrhage (SAH). Unfortunately, despite best medical efforts, SAH will be fatal in roughly 50% of the cases, with a significant percentage of patients dying before they even reach the hospital. Of survivors, approximately one half are left with permanent disability, for example, a stroke, which permanently compromises their independence and quality of life. Once an aneurysm ruptures, if it does not stop bleeding on its own within seconds, the patient generally dies. After an aneurysm has bled once, the risk of rebleeding is very high, and each hemorrhage carries at least a 50% mortality rate so urgent treatment is generally performed to prevent rebleeding. In addition, aneurysms are now being found prior to rupture as sophisticated imaging techniques such as magnetic resonance imaging, magnetic resonance angiography, and computerized tomographic angiography are gaining widespread use. These non-invasive techniques allow for the demonstration of an aneurysm before it bleeds, and their increasing use has led to the discovery of an unexpectedly significant number of patients with unruptured, asymptomatic lesions.

In general, there are two forms of treatment for a brain aneurysm, whether it has bled or not. Open microsurgery, a so-called craniotomy, with aneurysm clipping entails opening the skull and placing a metal clip, usually made from titanium, across the neck of the aneurysm to reconstruct the normal contour of the parent artery which harbors the aneurysm. Open clipping procedures have been performed for almost a century. This is the traditional, so-called "gold standard" method for treating an aneurysm of the brain. Once properly clipped, aneurysms rarely recur, and the patient is generally cured. If the aneurysm has already bled, there may be consequences of the initial hemorrhage, but the aneurysm cannot bleed again, and the patient is thus protected from the insult of a repeat hemorrhage. Over the past 50 years, repeatedly refined designs of increasingly pure titanium clips have been manufactured providing the neurovascular surgeon with numerous clip shape and size choices that can either singly or in combination address most, but not all, aneurysms.

The major alternative form of treatment for brain aneurysms is endovascular coiling. Coiling is a much newer technique that was introduced in the 1990's. A microcatheter is fed from a puncture site in the femoral or groin artery up into the carotid or vertebral arteries, and all the way into the aneurysm itself at the base of the brain. This is all done while watching the progress of the microcatheter on a fluoroscope using biplane digital subtraction angiography. Once the catheter tip is positioned inside the aneurysm, a tiny platinum wire is fed through the catheter into the aneurysm. The wire coils up on itself and fills the aneurysm so that when completed, the coiled aneurysm is essentially full of wire and no blood can enter the aneurysm from the main parent artery. This coil mass essentially acts as a physical barrier preventing blood from entering the aneurysm and reaching the wall of the aneurysm. Thereby, the aneurysm is prevented from rupturing.

Coiling of aneurysms has rapidly gained acceptance as an important technique in aneurysm treatment. It is minimally invasive, avoiding the need for an open brain operation, i.e. it avoids a craniotomy. The patients tend to recover more quickly and have less down time after the procedure compared with open surgery. Unfortunately, coiling works best for aneurysms with a narrow neck that will help prevent the coil mass from herniating back into the main artery, i.e. the parent artery. In wider necked aneurysms, such coil protruding into the main artery could result in blockage of blood supply through the main artery and subsequent stroke. In addition, many aneurysms will recur or regrow after coiling. As the blood pumps against the coil mass sitting in the aneurysm, it tends to "compact" the coils themselves out towards the dome of the aneurysm, and then blood flow can once again enter the aneurysm, and the patient is again at risk for bleeding from the thin wall of the aneurysm. Nevertheless, the great appeal and relative ease of coiling as opposed to open surgery has resulted in a substantial percentage of aneurysms being treated with endovascular coiling.

In general, aneurysm clips are comprised of two blades or arms that are parallel and opposed to each other in the resting position. A clip applying device which opens the clip blades is used to allow the clip, which can be opened and closed like a clothespin, to be applied to the aneurysm. As the clip is allowed to close, the blades return to the parallel, perfectly opposed position, collapsing the soft aneurysm between the blades. When applied properly down at the base of the aneurysm neck, the blades completely stop any blood flow into the now "empty sac" of the aneurysm which has been cured. When clipping an aneurysm, the surgeon relies on the softness of the wall of the aneurysm which allows the clip blades to close in opposition to one another. Anything that prevents the clip itself from closing properly may prevent proper clipping of an aneurysm. Because the blades of the clip have a strong so-called "closing strength" a force will be exerted against any such an obstructing item as the blades attempt to resume their resting, closed position. Those aneurysms that are not soft-walled represent the crux of the problem addressed by this development.

An aneurysm may not allow a clip to close properly because there is atheroma or calcium, which forms a hardening of the artery within the wall of the aneurysm itself, because there is organized hematoma or thrombus within the aneurysm itself, or because the aneurysm is filled with coils from a previous endovascular treatment. When traditional clips fail because of non-compliance of the aneurysm, a dangerous situation is created. The clip can slip back off the aneurysm, it can be forced down onto the neck of the aneurysm blocking flow through the main artery or its branches, or it can tear through the wall of the aneurysm with disastrous consequences. As coiling has become more common, and as coiling has been used increasingly for small, simple aneurysms, those aneurysms that are referred for open surgery are increasingly large and giant aneurysms with atheromatous, calcified walls, intraluminal thrombus, and previously coiled aneurysms in which the coils have failed. These are precisely the subgroups of aneurysms that are hardest to treat using conventional clip technology, for the reasons stated above. A better option for surgical aneurysm obliteration is clearly needed for these most difficult and challenging lesions.

As described above, aneurysms are generally treated with either clipping or coiling. The large and giant aneurysms are the ones most likely to have thick non-compliant walls, and these aneurysms represent a serious management challenge. Also, the growing number of previously coiled aneurysms that have failed and recurred is increasing exponentially. There are no optimal treatments for these lesions today. Some of these aneurysms can be clipped using very large, long clips that have a very high closing pressure. The aneurysms can be "crushed" with a forceps or clamp first to allow the clips to close, but this is a dangerous maneuver that can rupture the aneurysm or shower clot out of the aneurysm into the blood supply causing a stroke. Some aneurysms can be treated by temporarily stopping blood flow to the aneurysm, cutting the aneurysm open, and removing the thicker portion of the wall with any associated thrombus. The aneurysm can then be closed by over-sewing the opening, so-called aneurysmorrhaphy, or with very large clips. Unfortunately, stopping the blood flow to the aneurysm, even temporarily, may mean stopping the blood flow to the normal brain which can cause a stroke. Even if no stroke occurs from the temporary arterial occlusion, the wall of the aneurysm may be brittle or friable and may not be repairable once opened resulting in disaster.

Still other aneurysms require permanent occlusion of the entire involved artery, relying on collateral blood supply to prevent a stroke or performing a delicate brain bypass surgery to bring new blood supply to the part of the brain that was being fed by the artery that must be sacrificed. If the bypass is unsuccessful, the result is usually a severe stroke. Some aneurysms can be re-filled with coils, but many will only regrow yet again over time, at which point the problem may be even worse. Finally, some aneurysms can be wrapped with gauze to toughen the wall and decrease future risk of bleeding. This is the least reliable way to treat an aneurysm, and there is little data on long-term follow-up after wrapping. The aneurysm is essentially left unsecured with the potential for future bleeding.

In short, there are no good treatment methods currently available for these vexing lesions.

As described in detail above, all current treatment options are a high risk and dangerous. The complication rates including stroke and death rates in these patients are many times higher than in the patients with simple smaller aneurysms. This is simply a reflection of the limited available technology to treat these lesions. Because there is nothing better available, surgeons are forced to apply a technology that is not designed to treat properly these lesions in particular. Clips which depend on a soft, compliant aneurysm wall to close are generally not intended for and are no match for a giant, atheromatous aneurysm or an aneurysm full of coils.

Therefore, any new method designed to treat this subgroup of aneurysms will have to address the wall non-compliance that prevents traditional clips from closing properly. It should be able to address the problems of a thick wall as well as a mass of coils within the aneurysm, both of which will work against the closure of all standard aneurysm clips.

SUMMARY OF THE INVENTION

In accordance with the invention, a surgical clip comprises a first arm and a second arm, the first and second arms having first and second clamping surfaces facing each other, and the first and second arms being mounted for movement relative to each other, and further comprises a distance retaining device for keeping the first and second arms permanently spaced from each other.

Furthermore, in accordance with the invention, a surgical method for treating an aneurysm comprises: applying a surgical clip to the aneurysm, the clip comprising a first arm and a second arm, the first and second arms having first and second clamping surfaces facing each other for clamping the aneurysm therebetween, the first and second arms being mounted for movement relative to each other, and the first and second arms being kept permanently spaced from each other, wherein the aneurysm is clamped between the arms kept permanently spaced from each other.

DETAILED DESCRIPTION OF THE DRAWINGS

Although the invention is illustrated and described herein with reference to specific embodiments, the invention is not intended to be limited to the details shown. Rather, various modifications may be made in the details within the scope and range of equivalence of the claims and without departing from the invention.

The present invention relates to a surgical clip comprising a first arm and a second arm, the first and second arms having first and second clamping surfaces facing each other, and the first and second arms being mounted for movement relative to each other, and further comprising a distance retaining device for keeping the first and second arms permanently spaced from each other.

The surgical clip in accordance with the present invention is, in particular, designed in the form of a compression clip for the treatment of wider necked, atheromatous, thrombotic and/or previously coiled intracranial aneurysms. Its unique feature is that it comprises a distance retaining device for keeping the first and second arms permanently spaced from each other. In other words, in a closed position, the first and second arms which are also called clip blades do not rest in a parallel, perfectly opposed fashion. The distance retaining device allows separation of the blades by a preset so-called "opening distance" or "opening diameter" ("O.D."). Thus, in the closed position, the blades do not actually contact one another and may not be parallel to one another. Because the arms of the surgical clip never contact one another, there is no traditional measurement of a so-called "closing force" associated with the clip design according to the present invention. Rather, the amount of pressure applied to the aneurysm wall will depend on the amount of intervening tissue or material as well as the thickness and consistency of the wall itself.

It is advantageous for the distance retaining device to be designed such that in a basic position in which no extraneous forces are acting on the clip, the first and second arms are spaced from each other. Such a design avoids forcing the aneurysm into a flat pancake-like shape.

In accordance with a preferred embodiment of the invention, the surgical clip further comprises a restoring device which is arranged and constructed such that the first and second arms are movable away from each other against the restoring force exerted by the restoring device. The restoring device easily allows movement of the arms back into a basic position in which no extraneous forces are acting on the clip. For applying the surgical clip to the aneurysm to be treated the arms of the clips have only to be moved away from each other against the force of the restoring device, which allows automatic transfer of the surgical clip into a clamping position.

Preferably, the surgical clip further comprises a restoring device which is arranged and constructed such that the first and second arms are movable from the basic position to a spread out position in which the first and second arms are spaced further apart from each other than in the basic position against the restoring force exerted by the restoring device. The restoring device allows automatic transfer of the surgical clip from the spread out position back into the basic position.

Preferably, the restoring device is constructed such that in at least one of the spread out position and the basic position, the first and second arms are biased towards each other. Such a design of the clip diminishes or even eliminates the dangerous tendency of traditional clips to slip down, which could result in an occlusion or narrowing of the parent artery or branch artery or perforation of the blood vessel.

A particularly simple design of the clip is made possible by the restoring device comprising a spring coil.

Preferably, the spring coil comprises one to five windings. Depending on the number of windings, a closing force can be set when manufacturing the clip. In order to improve the stability of the clip, it is advantageous for the first and second arms and the restoring device to be made of one piece.

A possible twisting movement of the first and second arms relative to each another can be minimized by the surgical clip further comprising first and second connecting sections connected to the first and second arms, with the first connecting section penetrating the second connecting section.

A particularly simple construction of the clip is made possible by the second arm having a through-opening and the first arm penetrating the through-opening.

Preferably, the through-opening is in the form of a slit for guiding relative movement of the first and second arms in a clamping plane. Such a design allows easy perfect application of the clip to the aneurysm to be treated. Furthermore, a relative movement between the first and second arms can be perfectly guided.

In principle, it would be possible for the first and second arms to be movable relative to each other in parallel. In particular, for applying the surgical clip during a minimal invasive surgical procedure, it is advantageous for the first and second arms to be pivotable about a pivot axis.

Preferably, the pivot axis is defined by the restoring device. Such a design enables a very small and compact clip design.

It is advantageous for the surgical clip to further comprise a pivot joint defining the pivot axis. The pivot joint also allows guidance of a relative movement of the first and second arms.

A particularly simple design of the surgical clip is made possible by the pivot joint comprising a pivot pin defining the pivot axis.

In accordance with a preferred embodiment of the invention, the surgical clip comprises first and second clip parts, the first clip part comprising the first arm and the second clip part comprising the second arm. In particular, such a design makes it possible to choose different materials for constructing the surgical clip.

To enable an individual design for each of the clip parts, in particular, of the first and second arms, it is advantageous for the first and second clip parts to be of two-piece design.

In accordance with a further preferred embodiment of the invention, the surgical clip further comprises a locking device for locking the first and second arms in a position relative to each other. The locking device allows, in particular, locking of the first and second arms in a position, which might be defined as a locking position. Such a unique design of the clip diminishes or even eliminates the dangerous tendency of traditional clips to be inadvertently brought back into the spread out position, which would allow the clip to slip down the aneurysm.

Preferably, the locking device is of unidirectional design. This enables the surgical clip to be brought from a spread out position into a clamping position but not from the clamping position back into the spread out position. This allows a relatively simple application of the surgical clip to an aneurysm.

It is advantageous for the locking device to be designed such that the first and second arms are movable only from a spread out position to a clamping position, the first and second arms being spaced further from each other in the spread out position than in the clamping position, and the clamping position defining the basic position. In other words, the described preferred surgical clip design allows only a unidirectional movement of the first and second arms relative to each other from the spread out position to the clamping position.

In order to ensure that the surgical clip fits perfectly on the aneurysm it is advantageous for a distance between the first and second arms to be minimal in the clamping position.

Preferably, the locking device comprises locking elements arranged on at least one of the first and second arms, the locking elements engaging in a locking position in order to define the clamping position. The locking elements allow locking of the surgical clip in the clamping position, in particular, if the locking elements are designed to provide at least one of a positive and non-positive engagement of the locking elements.

A particularly simple design of the locking device is made possible by the locking elements being in the form of locking projections and locking receptacles. Preferably, the locking projections and the locking receptacles are designed to cooperate with one another.

The locking elements can easily engage each other if the locking elements are at least partially flexible or elastic. Such a design of the locking elements allows provision of a snap-fit connection for defining the clamping position.

Preferably, in the basic positions the first and second clamping surfaces extend parallel to each other. Such a design easily enables a desired opening distance or opening diameter to be defined between the arms of the surgical clip.

In accordance with a preferred embodiment of the invention, the first and second arms are curved. Such a unique design of the clip with the clip blades, at rest in the closed or clamping position, not sitting in the typical parallel opposition, diminishes or even eliminates the dangerous tendency of traditional clips to slip down, back off, remain perched in a precarious partially opened position and/or fail to close.

In order to perfectly fit around a wider-necked atheromatous, thrombotic and/or previously coiled intracranial aneurysm, the first and second arms are curved concavely with respect to one another. Such a design enables perfect enclosure the aneurysm to be treated.

In accordance with a further preferred embodiment of the invention, the surgical clip further comprises a stop device for limiting movement of the first and second arms towards each other. Such a design diminishes or even excludes the danger of rupturing the aneurysm with the clip.

It is advantageous for the stop device to define a spread out position in which a distance between the first and second arms is maximal. Thus, an undesired contact between the surgical clip and surrounding tissue which is usually rather weak can be minimized.

Moreover, it is expedient for the stop device to define a clamping position in which a distance between the first and second arms is minimal. A surgical clip comprising such a stop device can ensure that a desired opening diameter or opening distance between the clamping surfaces can be maintained, in particular, in the clamping position.

Furthermore, it is preferred if the stop device is designed such that the first and second arms are movable between a spread out position and a clamping position, the first and second arms being spaced further from each other in the spread out position than in the clamping position. Such a stop device is well-suited for defining both the spread out position and the clamping position.

In accordance with a further preferred embodiment of the invention, the surgical clip further comprises a stop device for limiting movement of the first and second arms away from each other. Such a stop device is preferably effective in the clamping position in order to ensure that the surgical clip backs off the aneurysm to which it is applied.

Moreover, in accordance with another preferred embodiment of the invention, the surgical clip further comprises first and second clamping elements arranged on the first and second clamping arms or surfaces. The first and second clamping elements can increase a gripping action between the surgical clip and the aneurysm in order to minimize the dangerous tendency of the clip to slip down the aneurysm.

In order to be perfectly applied to the aneurysm, the clamping elements define first and second clamping element surfaces facing each other. This allows the clamping elements to surround or enclose the aneurysm in a desired manner.

Preferably, the first and second clamping element surfaces are larger than the first and second clamping surfaces. Such a design allows, in particular, improvement of a gripping action of the surgical clip. In particular, the first and second clamping element surfaces can be larger in width than the first and second clamping surfaces.

It is advantageous for the first and second clamping element surfaces to rest against each other in the basic position. This ensures that the clamping surfaces of the clip arms remain at the desired distance from each other.

In order to provide a perfect fit of the surgical clip in the region of the aneurysm it is advantageous for the first and second clamping elements to be in the form of pads.

Preferably, the first and second clamping elements are of flexible or elastic design. Such a clamping element design allows an individual adjustment and a perfect fit of the surgical clip for treating the aneurysm.

In accordance with a further preferred embodiment of the surgical clip, the first and second clamping elements are made from at least one of a plastic material or a gel. Clamping elements made from the aforementioned materials can easily adapt to any shape of an aneurysm.

The invention further relates to a surgical method for treating an aneurysm, the method comprising: applying a surgical clip to the aneurysm, the clip comprising a first arm and a second arm, the first and second arms having first and second clamping surfaces facing each other for clamping the aneurysm therebetween, the first and second arms being mounted for movement relative to each other, and the first and second arms being kept permanently spaced from each other, wherein the aneurysm is clamped between the arms kept permanently spaced from each other.

Such an improved surgical method for treating an aneurysm enables the dangerous tendency of traditional clips to slip down or back off, to be diminished or even eliminated.

Preferably, the surgical method is carried out by applying the clip to one of a wider-necked, atheromatous, thrombotic, and previously coiled intracranial aneurysm. In particular, the proposed surgical method is advantageous for the aforementioned indications compared to applying known surgical clips or coiling the aneurysm.

Preferably, a microdissection is carried out in the region of the aneurysm and the necessary distance between the first and second arms in a closed position of the clip is estimated or measured. These steps of the surgical method help to improve the success of the treatment since it is possible to choose a surgical clip of a size which fits the aneurysm best.

It is advantageous for the clip to be inserted into the patient's body through an access provided therefor.

It is advantageous for the clip to be opened and applied across one of the base and neck of the aneurysm. The base or the neck are perfect locations for applying the clip in order to treat the aneurysm in a desired manner.

The clip can be applied to the aneurysm in a particularly simple manner if the clip is opened and applied using a clip applying device. In particular, if the clip is rather small, using a clip applying device enables insertion of the surgical clip and application of it to the aneurysm in a defined manner.

In order to improve applying the clip to the aneurysm it is advantageous for the clip to be allowed to close gradually. This allows gradual adopting of the clip to the aneurysm to be treated.

Preferably, the clip is allowed to compress an aneurysm wall against one of atheroma, thrombus and coils, and then against the opposite aneurysm wall. This leads to a perfect fit of the surgical clip on the aneurysm in order to reconstruct the normal contour of the blood vessel.

In order to simplify the application of the clip to the aneurysm it is preferred if the first and second arms are moved away from each other against a restoring force exerted by the clip.

It is advantageous for the first and second arms to be locked in a clamping position relative to each other. Thus, it can be ensured that the surgical clip maintains the well-defined clamping position.

Preferably, in the clamping position a distance between the first and second arms is minimal. An adjustment of the surgical clip in the described manner ensures that the aneurysm wall is not completely clamped off so that rupture thereof can be avoided.

It is expedient if the first and second arms of the surgical clip are curved. Applying a surgical clip with curved arms allows a perfect fit of the clip of the aneurysm because the arms can surround the aneurysm, in particular, a base or a neck of the aneurysm, in a natural way.

In accordance with a further preferred alternative of the surgical method in accordance with the present invention, first and second clamping elements are arranged on the first and second clamping surfaces. The first and second clamping elements can be designed such that they fit perfectly around a base or a neck of an aneurysm.

The aneurysm can be easily clamped between the clamping elements if they define first and second clamping surfaces facing each other.

A large-area compression can be easily achieved if a surgical clip is applied which has first and second clamping element surfaces that are larger than the first and second clamping surfaces.

Preferably, in a basic position the first and second clamping element surfaces rest against each other. Thus, it can be achieved that the clamping surfaces of the first and second arms are kept at the desired distance from each other.

Compression forces exerted by the surgical clip on the aneurysm can be individually adjusted if the first and second clamping elements are in the form of pads. Moreover, such a surgical clip can be easily manufactured.

The surgical method allows an individual adjustment of the surgical clip on the aneurysm if the first and second clamping elements are of flexible or elastic design.

In order to minimize the danger of a rupture of the aneurysm wall it is advantageous for the first and second clamping elements to be made from at least one of a plastic or a gel.

Figure 1:
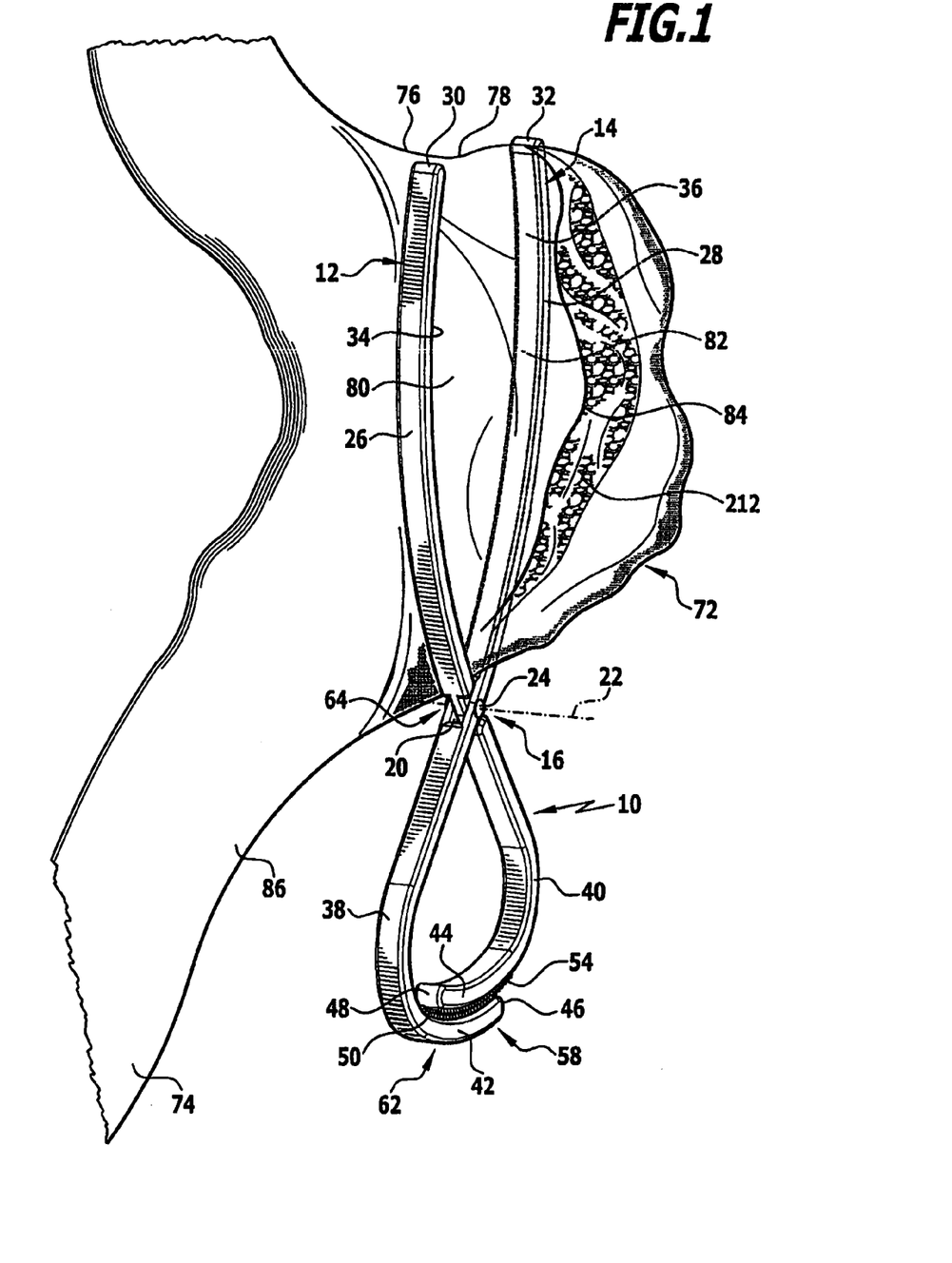
FIG. 1 shows a perspective view of a first embodiment of a surgical clip applied to an aneurysm.
Figure 2:
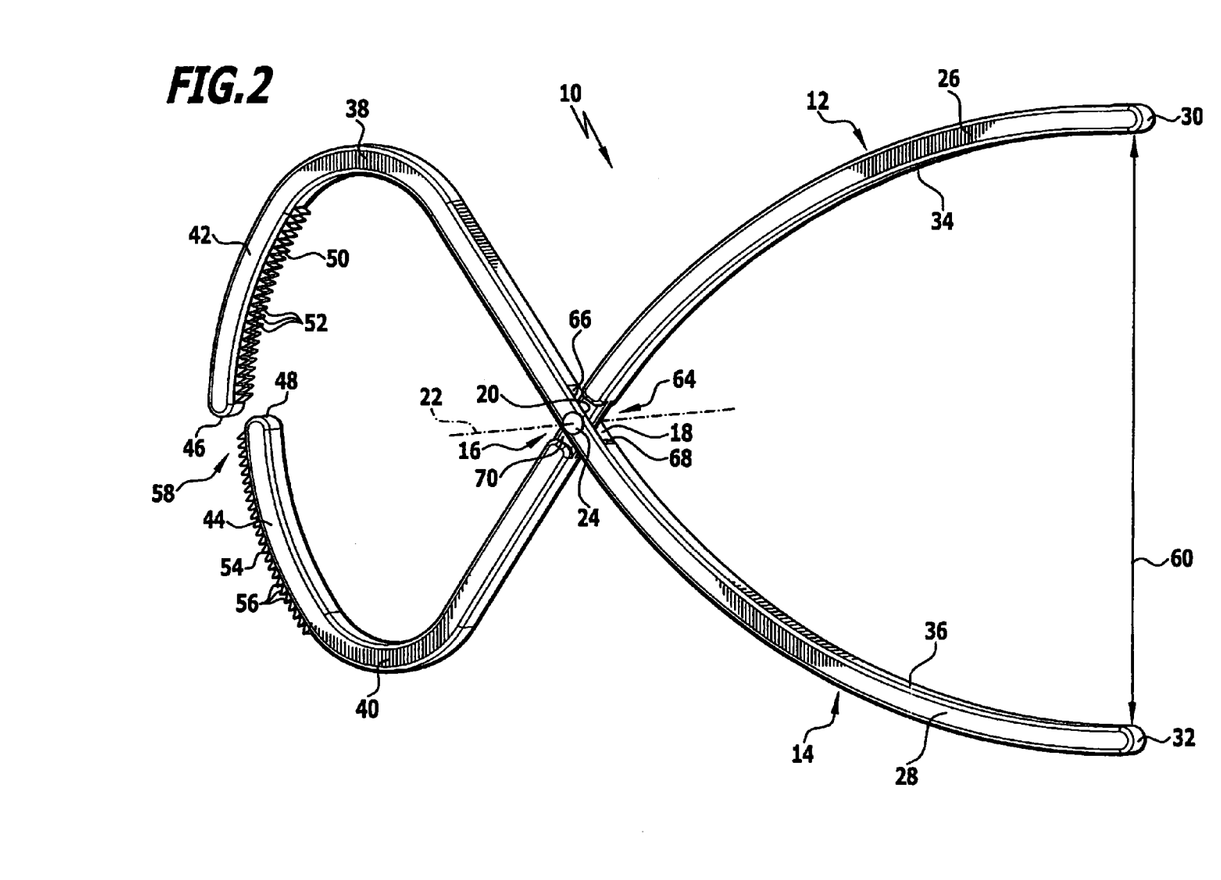
FIG. 2 shows a perspective view of the surgical clip shown in FIG. 1 in a spread out position.
Figure 3:
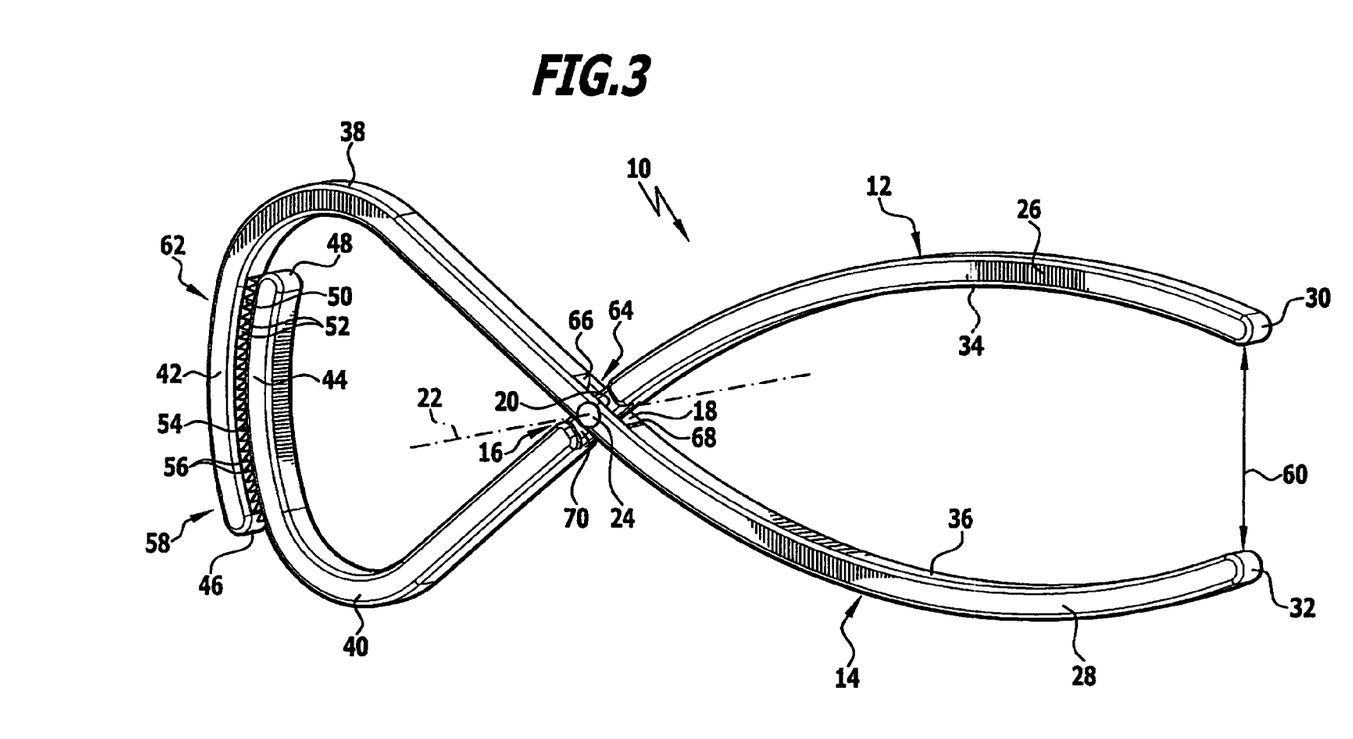
FIG. 3 shows the surgical clip shown in FIG. 2 in a clamping position.

FIGS. 1 to 3 show a first embodiment of a surgical clip in the form of an aneurysm clip given the overall reference numeral 10. The clip 10 comprises first and second clip parts 12, 14 which are linked together by means of a pivot joint 16.

The second clip part 14 comprises a through-opening 18 in the form of a slit 20 which allows the first clip part 12 to penetrate the through-opening 18. The slit 20 defines a clamping plane which is perpendicular to a pivot axis 22 defined by a pivot pin 24 which is inserted in a bore extending coaxially through both the first and second clip parts 12, 14 in the region of the connection portion. Each of the clip parts 12, 14 defines an arm 26, 28 which can also be called blades. The arms 26, 28 extend from the pivot joint 16 towards distal ends 30 and 32. Cross sections of the arms 26, 28 are rectangular-shaped. Side faces of the arms 26, 28 facing towards each other define clamping surfaces 34, 36. The clamping surfaces 34, 36 may be structured in order to improve a gripping action thereof. The clamping surfaces 34, 36 and the arms 26, 28 are curved concavely with respect to each other.

Proximal portions 38, 40 defined by the first and second clip parts 12, 14 and extending from the pivot joint 16 in a proximal direction are also concavely curved with respect to one another. End portions 42 and 44 of the proximal portions 38 and 40 extend towards proximal ends 46, 48 of the first and second clip parts 12, 14. The end portions 42, 44 are constructed in the form of a circular arc arranged coaxially with respect to the pivot axis 22.

An inner surface of the end portion 42 facing towards the pivot axis 22 carries a plurality of locking elements 50 in the form of locking teeth 52. A side surface of the end portion 44 facing away from the pivot axis 22 carries a plurality of locking elements 54 which are designed in the form of locking teeth 56. The locking teeth 56 are arranged such that they can engage with the locking teeth 52. The locking elements 50 and 54 jointly define a locking device 58 which is of unidirectional design.

In a basic position of the surgical clip 10 the locking elements 50, 54 are not engaged. A distance 60 which corresponds to a maximum opening distance between the distal ends 30 and 32 is maximal in this basic position. Due to the unidirectional design of the locking device 58 it is only possible to pivot the arms 26 and 28 towards each other in order to reduce the distance 60 between the distal ends 30 and 32. At the same time, the teeth 52 and 56 mesh with each other. Due to the unidirectional design of the locking device 58 it is only possible to pivot the arms 26, 28 towards each other. The design of the teeth 52 and 56 prevents pivotal movement of the proximal portions 38, 40 away from each other. In order words, the locking device 58 is designed such that the first and second arms 26, 28 are movable only from a spread out position which is schematically shown in FIG. 2 to a clamping position shown by way of example in FIGS. 1 and 3.

The first and second arms 26, 28 are spaced further from each other in the spread out position than in the clamping position. Moreover, the clamping position in which the distance 60 becomes minimal defines a basic position of the aneurysm clip 10. The locking device 58 in cooperation with the smaller radius of the proximal portions 38, 40 adjacent to the end portions 42, 44 define a distance retaining device 62 for keeping the first and second arms 26, 28 permanently spaced from each other. The distance 60 in the basic position of the clip 10 as shown in FIGS. 1 and 3 defines a preset "opening distance" or "opening diameter" abbreviated as "O.D.".

The distance retaining device 62 and the locking device 58 form a raster mechanism which holds the clamp in defined positions. With this raster mechanism it is possible to close the clip 10 in small increments to the position where it rests perfectly on a neck 78 of the aneurysm 72 without slipping down the artery 88.

The aneurysm clip 10 further comprises a stop device 64 for defining the spread out position in which the distance 60 is maximal. The stop device 64 comprises stop surfaces 66 and 68 defined by inner side surfaces of the slit 20 which face towards each other and extend generally parallel to the pivot axis. Both in the spread out position and in the basic position the weakened joint portion 70 of the first clip part 12 forming a connection portion either abuts with its distal portion on one of the stop surfaces 66 and 68.

The aneurysm clip 10 is used for treating an aneurysm 72 of a blood vessel 74, in particular, a blood vessel 74 supplying blood flow to the brain of a patient. The method is described in further detail below.

After thorough microdissection of the local anatomy in the region of the aneurysm 72, the necessary O.D. of the clip 10 in its closed position or clamping position is estimated or measured either based on the preoperative imaging studies or using a fine, specially calibrated measuring tool. The clip 10 is then introduced into the field, applied across the base 76 or neck 78 of the aneurysm 72 using a specialized clip applying device not shown in the figures. The clip 10 is then allowed to close gradually, gently compressing an aneurysm wall 80 against atheroma and/or thrombus and/or coils, and then against the opposite aneurysm wall 82. This effectively "sandwiches" any intervening material like clot, coil, atheroma and the like between the two walls 80, 82 of the aneurysm 72, taking advantage of the intervening material to close an opening 84 into the aneurysm 72, eliminating blood flow into the aneurysm 72 itself.

The unique design of the clip 10 with the arms 26, 28 or clip blades, which are at rest in the closed position and not sitting in the typical parallel opposition as is the case with clips known from the prior art, diminishes or even eliminates the dangerous tendency of traditional clips to slip down, thereby occluding or narrowing a parent artery or branch artery, or perforating the vessel 74, back off, remain perched in a precarious partially open position, and/or fail to close. The clip 10 is generally applied several millimeters above the true interface between the parent artery 86 and the aneurysm 72 to avoid narrowing the true parent artery. It is generally recommended that an intraoperative angiogram be employed to assess the adequacy of aneurysm obliteration and preservation of all critical neurovascular structures, although this may be left at the surgeon's discretion. In select cases, when completely closing the aneurysm neck 78 is not safe or possible due to extreme calcification or atheroma in the aneurysm walls 80, 82 or due to other unique consideration, the clip 10 can be used to narrow the neck 78 of a wide-necked aneurysm 72 allowing for more aggressive and possible curative coiling. In the setting of very complicated aneurysms 72, the clip 10 can be used as a so-called "pilot" clip, to allow for partial aneurysm closure, allowing for more aggressive dissection around the aneurysm to be followed by more definitive clipping.

In summary, all current known aneurysm clip designs incorporate preferably parallel blades that oppose each other at rest to provide a closing force that brings together the generally compliant walls 80, 82 of a simple brain aneurysm 72. In sharp contrast, the so-called "compression clip" in the form of the aneurysm clip 10 described above uses arms 26, 28 that are not opposed at rest, sandwiching the walls 80, 82 against the intervening material contained within the aneurysm 72 or within the walls 80, 82 themselves to prevent blood from flowing into the aneurysm 72. This completely novel design addresses the difficulties that traditional clips face when attempting to close a thick-walled aneurysm 72 with intraluminal clot, thrombus, or coils. Instead of trying to force the aneurysm into a flat "pancake-like" shape, the compression clip 10 takes advantage of the natural curvature of the aneurysm wall 80, 82 as well as the firm material within the aneurysm wall 80, 82 and within the aneurysm 72. This intervening material becomes "part of the solution" with the compression clip 10 as opposed to being "part of the problem" with traditional clips.

The aneurysm clip 10 is preferably made from a biocompatible material, in particular, a biocompatible metal such as titanium or an implant steel.

Figure 4:
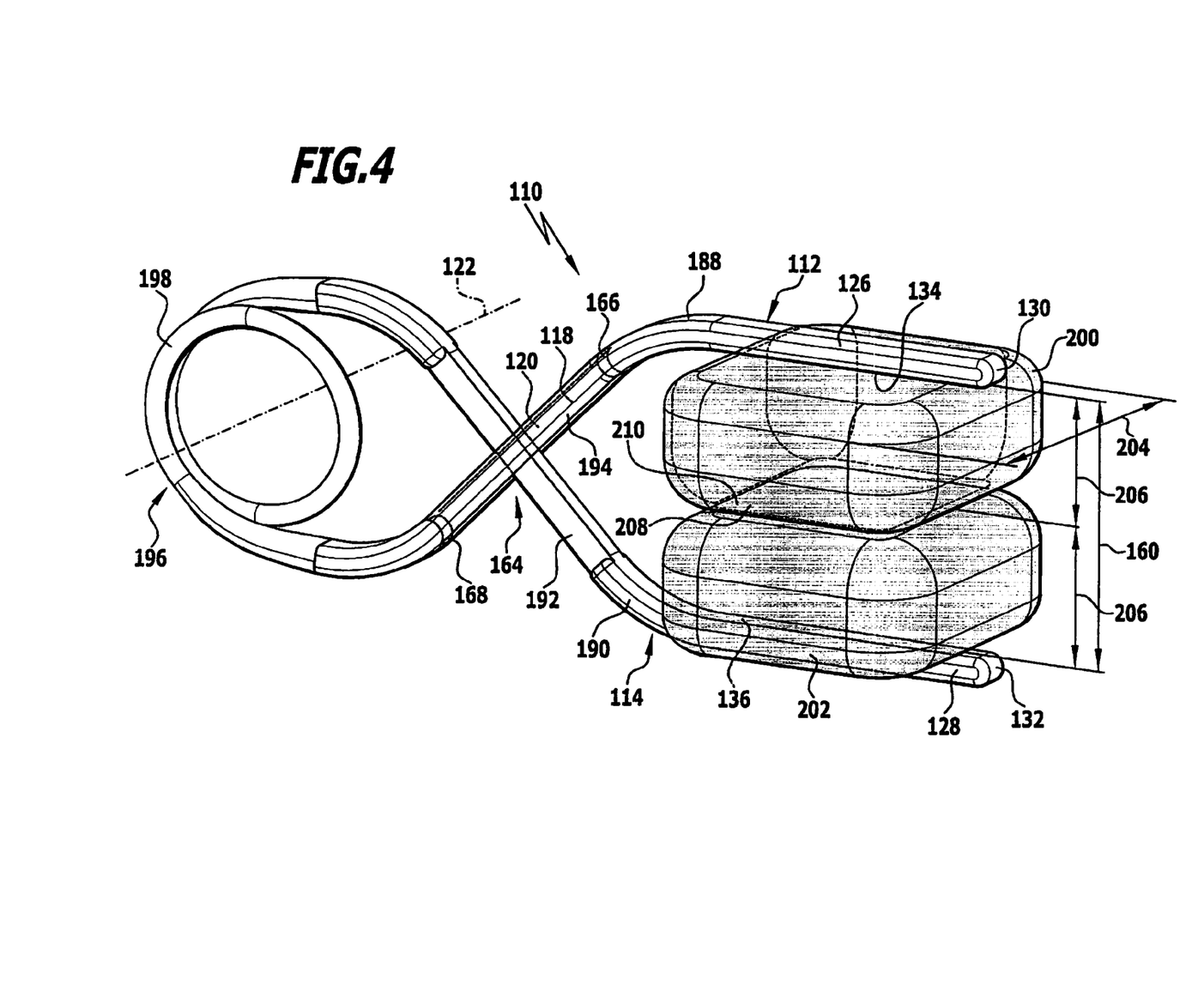
FIG. 4 shows a further embodiment of a surgical clip in a basic position.

A further embodiment of an aneurysm clip designated by the overall reference numeral 110 is shown in FIG. 4. The clip 110 is made from one piece and comprises clamping arms 126 and 128 which extend parallel with respect to each other in a basic or clamping position. A distance 160 between distal ends 132 of the arms 126, 128 is minimal in the clamping position.

Proximal end areas 188 and 190 adjoining the arms 126 and 128 are curved towards each other so that a first crossing portion 192 extending from the end area 190 penetrates a through-opening 118 in the form of a slit 120 in a second crossing portion 194 connected to the end area 188. End surfaces of the slit 120 facing each other form stop surfaces 166, 168 of a stop device 164 which defines both a maximum and a minimum distance 160 in a spread out position and a compressed or closed position.

The crossing portions 192 and 194 are connected by means of a restoring device 196 in the form of a coil spring 198 having about 1.5 windings. A center of the spring coil 198 defines a pivot axis 122 which extends perpendicular to a clamping plane defined by the slit 120. The cross sections of the arms 126 and 128 are of rectangular shape.

Clamping surfaces 134 and 136 of the arms 126, 128 carry first and second clamping elements 200, 202 which are of cuboidal shape. A width 204 of the clamping elements 200 and 202 is about five to ten times longer than a width of the arms 126, 128 parallel to the pivot axis 122. A thickness 206 of the clamping elements 200, 202 corresponds to 50% of the distance 160 in the closed or basic position of the clip 110. This results in a direct contact of the substantially planar clamping element surfaces 208 and 210 of the clamping elements 200 and 202 facing each other. The clamping elements 200 and 202 are designed in the form of pads made from a preferably flexible or elastic material as, for example, a plastic or a gel.

The method for treating the aneurysm 72 with the clip 110 corresponds to the method described above in connection with the clip 10. The clamping elements 200 and 202 perfectly fit the neck 78 of the aneurysm 72 although the arms 126, 128 are not curved. The flexible and/or elastic pads forming the clamping elements 200 and 202 automatically adapt to the negative form of the aneurysm 72 with the same result as the application of the aneurysm clip 10 as outlined above.

In the closed position of the clip 110 the clamping elements 200 and 202 rest against each other with their clamping element surfaces 208 and 210, preferably with a minimal closing force applied to them. When the clip 110 is placed around the neck 78 of the aneurysm 72 the clamping elements 200 and 202, preferably in the form of gel pads enclose the aneurysm neck 78 and contour the form of the intervening material 212 inside the aneurysm 72. This provides for a perfect closing of the aneurysm 72 with an equal closing force at each point. In order to offer a certain closing force the movement of the clip 110 is blocked at the slit 120 by introducing a blocking element, not shown in the drawings, into the slit 120 in order to force the crossing portion 192 against one of the stop surfaces 166 and 168.

Figure 5:
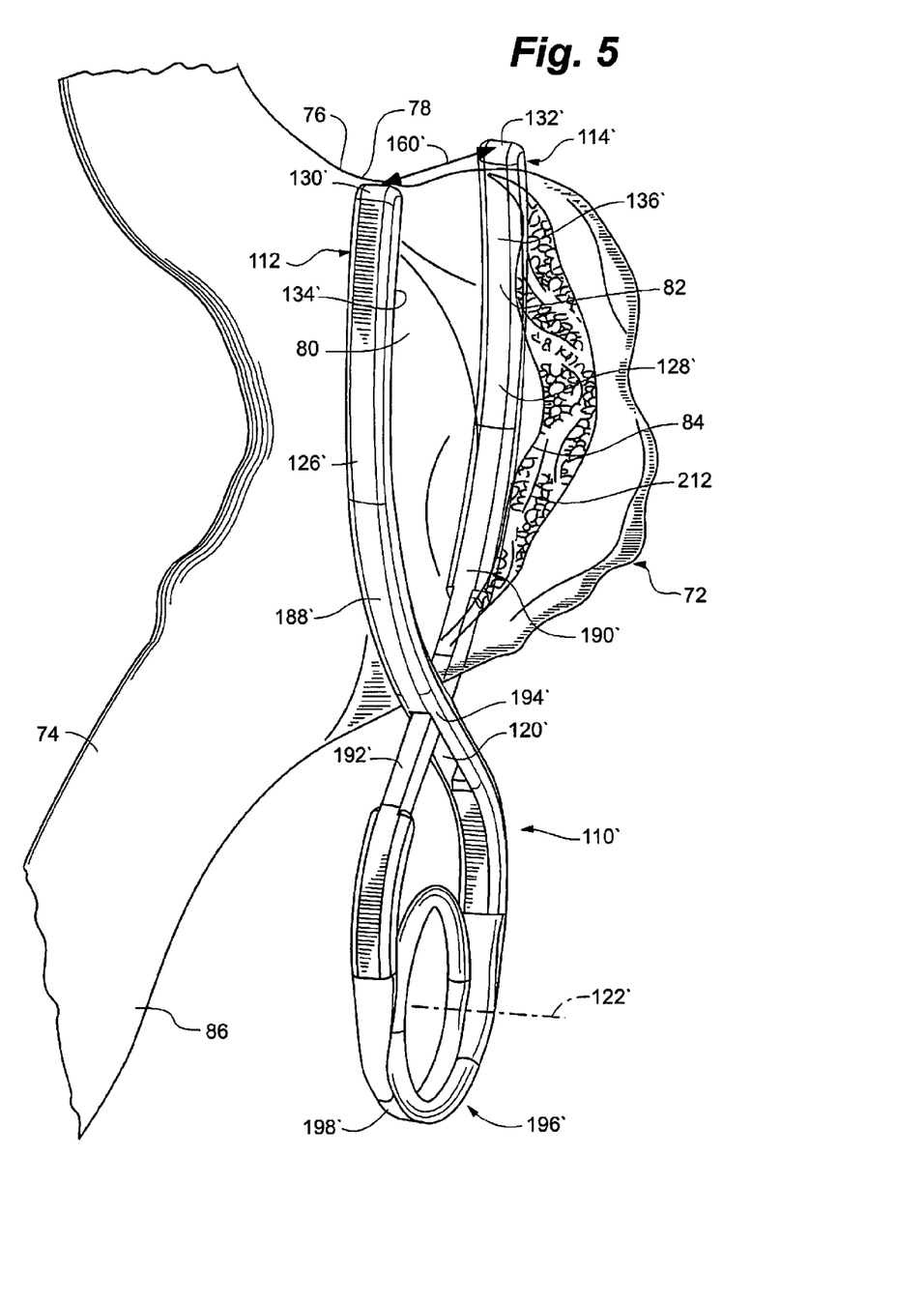
FIG. 5 shows a perspective view similar to FIG. 1 of a further embodiment of a surgical clip applied to an aneurysm.
Figure 6:
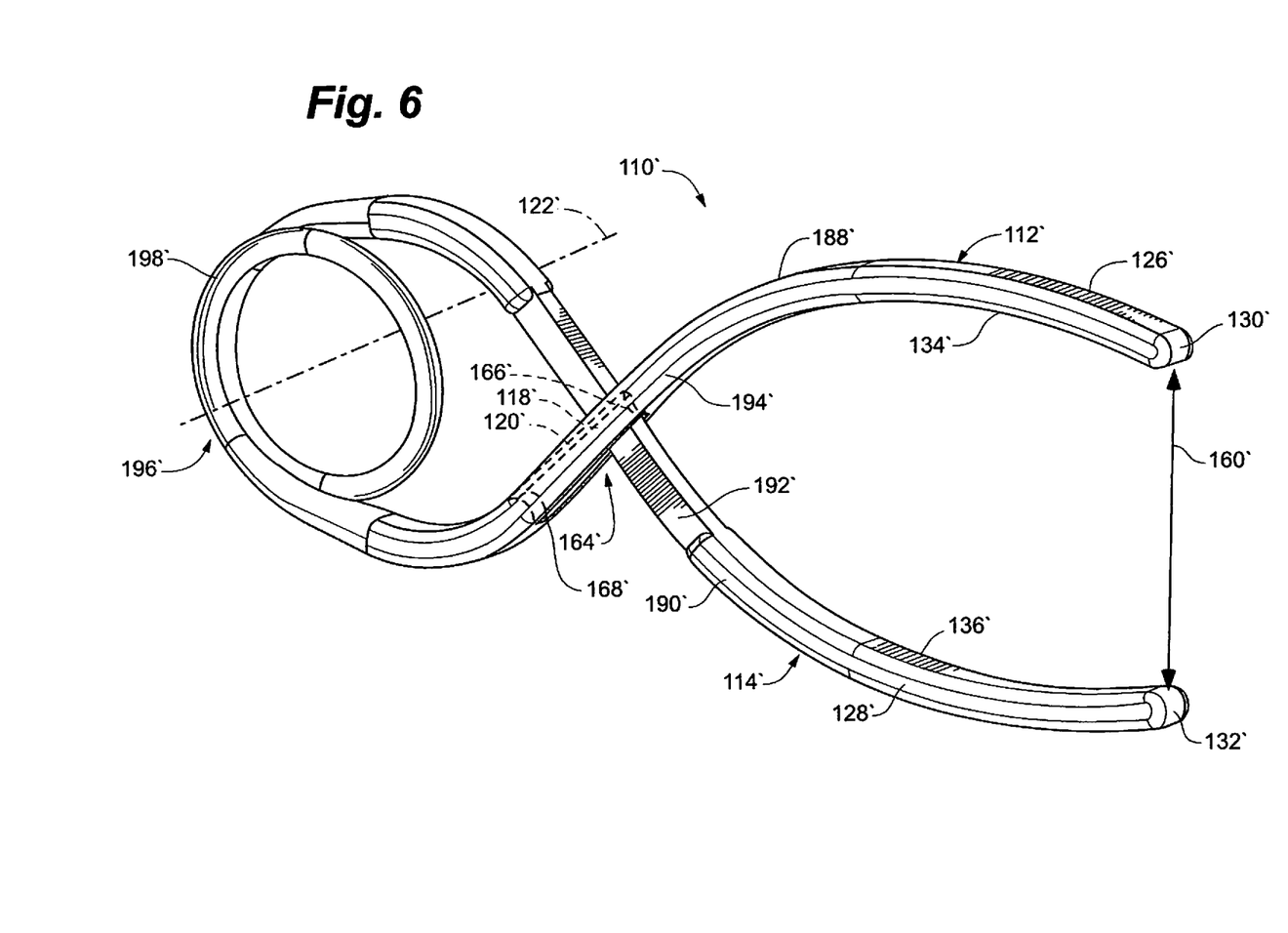
FIG. 6 shows a perspective view of the surgical clip shown in FIG. 5 in a basic position.

A further embodiment of an aneurysm clip is designated by the overall reference numeral 110' and shown schematically in FIGS. 5 and 6. The clip 110' is also made from one piece. However, in contrast to the arms 126 and 128 of the clip 110 the arms 126' and 128' are concavely curved with respect to each other like the arms 126 and 128 of the clip 10 are. Clamping surfaces 134' and 136' of the arms 126' and 128' may be structured in order to enhance a gripping action thereof. Moreover, the arms 126' and 128' do not carry clamping elements as the arms 126 and 128 do.

Other parts and portions of the clip 110' which are similar or identical in their design to parts and portions of the clip 110 are designated in the figures by identical reference numerals supplemented by a prime.

Thus, a further embodiment of an aneurysm clip designated by the overall reference numeral 110' is shown in FIGS. 5-6. The clip 110' is made from one piece and comprises clamping arms 126' and 128' which extend parallel with respect to each other in a basic or clamping position. A distance 160' between distal ends 132' of the arms 126', 128' is minimal in the clamping position.

Proximal end areas 188' and 190' adjoining the arms 126' and 128' are curved towards each other so that a first crossing portion 192' extending from the end area 190' penetrates a through-opening 118' in the form of a slit 120' in a second crossing portion 194' connected to the end area 188'. End surfaces of the slit 120' facing each other form stop surfaces 166', 168' of a stop device 164' which defines both a maximum and a minimum distance 160' in a spread out position and a compressed or closed position. Thus, crossing portion 192' is in abuttable engagement with stop surface 166' or 168' at minimum or maximum distance 160' respectively.

The crossing portions 192' and 194' are connected by means of a restoring device 196' in the form of a coil spring 198' having about 1.5 windings. A center of the spring coil 198' defines a pivot axis 122' which extends perpendicular to a clamping plane defined by the slit 120'. The cross sections of the arms 126' and 128' are of rectangular shape.

The application method for the clip 110' corresponds to the application method as described above in connection with clips 10 and 110.

The primary unique feature of the clip 110' is that in its closed position the arms 126' and 128' do not rest in a parallel, perfectly opposed fashion. Rather, in the resting/closed position of the clip 110' the arms 126' and 128' are separated by a preset "opening distance" (O.D.) which corresponds to distance 160'. Moreover, the arms 126' and 128' may be gently bowed inward, i.e. concavely towards each other to match the rounded shape of most intracranial aneurysms 72. Thus, in the closed positions, the blades or arms 126' and 128' do not actually contact each other and may not be parallel to one another. It has been noted that, because the arms 126', 128' never contact each other, there is no traditional measurement of a so-called "closing force" associated with this clip design. Rather, the amount of pressure applied to the aneurysm walls 80, 82 will depend on the amount of intervening tissue/material 212 as well as the thickness and consistency of the walls 80, 82 themselves. In order to offer a certain closing force the movement of the clip parts 112' and 114' may be blocked at the through-opening 118' with a spring tension remaining between the arms 126' and 128'.

The clips 110 and 110' are also made from a biocompatible material which enable leaving the clips 110 and 110' inside a patient's body.

All the above-described clip designs allow closing of an aneurysm 72 with intervening material, for example, coils, thrombus or calcification in its neck area without the risk of closing the supporting artery 86 partially or completely. The closing of the aneurysm 72 is achieved using the above-described different embodiments of the invention in the form of clips 10, 110 and 110' which have in common that their arms are not totally closed in the respective clamping positions. All the described clips leave the intervening material inside the aneurysm 72 and offer a surgeon the opportunity to leave the aneurysm 72 intact. Furthermore, it is not necessary to temporarily clip the supporting artery 86 with the risk of inducing small ischemic areas which are supported by small vessels branching off from the temporarily clipped artery 86.

The invention claimed is:

1. An implantable aneurysm clip, comprising:
a first arm and an opposed second arm, said first and second arms having corresponding opposed first and second clamping surfaces facing each other, and said first and second arms being movable relative to each other, the first and second clamping surfaces being dimensioned to grip the aneurysm;
the first and second clamping surfaces being shiftable between a first, preselected, open resting position wherein the first and second clamping surfaces are separated by a first distance and a second open position wherein the first and second clamping surfaces are separated by a second distance, the second distance being greater than the first distance and the first and second clamping surfaces being biased toward the first position by a biasing force;
the aneurysm clip further comprising first and second connecting sections connected to said first and second arms, wherein said first connecting section penetrates said second connecting section and is movable in a slit like opening; and
a stop device that inhibits movement of said first and second arms towards each other beyond the first position, the stop device comprising an abuttable engagement between a stop surface at an end of the slit like opening and the first connecting section when the first and second clamping surfaces are in the first, preselected, open resisting position wherein the first and second clamping surface are separated by the first distance.

2. The implantable aneurysm clip of claim 1, further comprising a restoring device that provides the biasing force toward the first position from the second position.

3. The implantable aneurysm clip of claim 2, wherein the restoring device comprises a spring.

4. The implantable aneurysm clip of claim 2, wherein the restoring device comprises a spring coil.

5. The implantable aneurysm clip of claim 4, wherein the spring coil comprising about one and one half spring windings.

6. The implantable aneurysm clip of claim 3, wherein the spring, the first arm and the second arm together form a unitary structure.

7. The implantable aneurysm clip of claim 1, wherein, in the first position, said first and second clamping surfaces extend generally parallel to each other.

8. The implantable aneurysm clip of claim 1, wherein, said first and second clamping surfaces are curved.

9. The implantable aneyurysm clip of claim 1, further comprising a second stop device the inhibits movement of said first and second arms away from each other beyond the second position.

* * * * *